United States Patent
Gazzelli et al.

(10) Patent No.: US 10,660,982 B2
(45) Date of Patent: May 26, 2020

(54) CONTAINER FOR STERILISING OBJECTS AND STERILISING SYSTEM COMPRISING SAID CONTAINER

(71) Applicant: GRATZUP CORP., New York, NY (US)

(72) Inventors: Mauro Gazzelli, Bissone (CH); Paolo Davide Curradini, Gardone Riviera (IT)

(73) Assignee: Gratzup Corp., New York, NY (US)

( * ) Notice: Subject to any disclaimer, the term of this patent is extended or adjusted under 35 U.S.C. 154(b) by 379 days.

(21) Appl. No.: 15/302,156

(22) PCT Filed: Mar. 27, 2015

(86) PCT No.: PCT/IB2015/052274
§ 371 (c)(1),
(2) Date: Oct. 5, 2016

(87) PCT Pub. No.: WO2015/155625
PCT Pub. Date: Oct. 15, 2015

(65) Prior Publication Data
US 2017/0021047 A1    Jan. 26, 2017

(30) Foreign Application Priority Data

Apr. 10, 2014    (IT) .............................. VI2014A0101

(51) Int. Cl.
*A61L 2/26*    (2006.01)
*A61L 2/04*    (2006.01)
(Continued)

(52) U.S. Cl.
CPC .................................... *A61L 2/26* (2013.01);
*A61L 2/04* (2013.01); *A61L 2/18* (2013.01);
*B65D 11/06* (2013.01);
(Continued)

(58) Field of Classification Search
CPC ..... A61L 2/04; A61L 2/18; A61L 2/26; A61L 2202/23; A61L 2202/24; B65D 11/02;
(Continued)

(56) References Cited

U.S. PATENT DOCUMENTS 785,591 A * 3/1905 Conez ....................... A47F 3/00
                                                211/85.4
1,896,976 A * 2/1933 Schifferdecker ......... G07D 9/02
                                                15/185

(Continued)

FOREIGN PATENT DOCUMENTS

| EP | 1 555 034 S1 | 7/2005 |
| GB | 2 048 676 A1 | 12/1980 |
| WO | 2010/142664 A1 | 12/2010 |

OTHER PUBLICATIONS

International Search Report and Written Opinion dated Sep. 1, 2015, issued in PCT Application No. PCT/IB2015/052274, filed Mar. 27, 2015.

*Primary Examiner* — Avinash A Savani
*Assistant Examiner* — Martha M Becton
(74) *Attorney, Agent, or Firm* — Fish & Richardson P.C.

(57) ABSTRACT

A container for sterilising objects, includes: a hollow body with mainly longitudinal development and closed at one end by a bottom, the hollow body being provided at the opposite end with an opening in proximity to which there is a first connection area; a substantially tubular body provided, in proximity to its ends, respectively with a second and a third connection area, each one of which is suited to be alternatively coupled with the first connection area of the hollow body. The container furthermore includes a shaped cover provided, at the level of its inner side walls, with a fourth connection area suited to be coupled with one of the connection areas of the tubular body and with the hollow body; a support is arranged inside the tubular body and in prox- (Continued)

imity to one of its ends, the support being configured so as to support one or more objects to be sterilised; a maximum pressure valve applied to the hollow body.

13 Claims, 5 Drawing Sheets

(51) Int. Cl.
*A61L 2/18* (2006.01)
*B65D 8/00* (2006.01)
*B65D 25/00* (2006.01)
*B65D 25/10* (2006.01)

(52) U.S. Cl.
CPC .......... *B65D 25/10* (2013.01); *A61L 2202/23* (2013.01); *A61L 2202/24* (2013.01)

(58) Field of Classification Search
CPC ................................................. B65D 11/06; B65D 11/10; A61J 9/008; A61J 9/085; A61J 9/00; F24S 20/30; F24S 23/70; F24S 23/71
See application file for complete search history.

(56) References Cited

U.S. PATENT DOCUMENTS

| | | | | |
|---|---|---|---|---|
| 2,721,552 A * | 10/1955 | Nosik | B65D 51/2814 | 206/222 |
| 2,773,591 A * | 12/1956 | Jensen | B65D 25/08 | 206/220 |
| 2,786,769 A * | 3/1957 | Greenspan | A61J 9/00 | 206/221 |
| 2,843,281 A * | 7/1958 | Gallois | A61J 9/00 | 215/11.1 |
| 2,994,318 A * | 8/1961 | Lee | A47J 27/08 | 126/681 |
| 3,025,851 A * | 3/1962 | Steinberg | F24S 20/30 | 126/682 |
| 3,106,201 A * | 10/1963 | Steinberg | F24S 23/00 | 126/682 |
| 3,144,152 A * | 8/1964 | Kopp | A47J 47/04 | 215/6 |
| 3,239,429 A * | 3/1966 | Menolasino | C12Q 1/22 | 116/207 |
| 3,314,563 A * | 4/1967 | Mounier | B65D 25/082 | 206/221 |
| 3,963,125 A * | 6/1976 | Baggott | A47B 31/00 | 211/126.15 |
| 4,024,952 A * | 5/1977 | Leitz | B65D 51/2878 | 206/221 |
| 4,083,357 A * | 4/1978 | Fischer | F24S 20/30 | 126/682 |
| D256,656 S * | 9/1980 | Naccach | D7/324 | |
| 4,262,660 A * | 4/1981 | Ilich | F24S 20/30 | 126/682 |
| 4,281,644 A * | 8/1981 | Chiles | F24S 20/30 | 126/682 |
| 4,305,504 A * | 12/1981 | Bredal | B65D 11/10 | 206/467 |
| 4,376,096 A * | 3/1983 | Bowen | A61L 2/04 | 219/441 |
| 4,416,257 A * | 11/1983 | Bale | F24S 40/58 | 126/610 |
| 4,442,828 A * | 4/1984 | Takeuchi | F24S 20/30 | 126/681 |
| 4,463,684 A * | 8/1984 | Klungle | A47B 43/00 | 108/91 |
| 4,616,754 A * | 10/1986 | Heinzl | B65D 11/10 | 211/126.15 |
| 4,779,722 A * | 10/1988 | Hall | A61J 1/2093 | 206/219 |
| 4,848,320 A * | 7/1989 | Burns | F24S 30/425 | 126/682 |
| 4,848,608 A * | 7/1989 | Anderson | A47B 57/10 | 211/71.01 |
| D306,952 S * | 4/1990 | Goeman | D24/199 | |
| 5,213,776 A * | 5/1993 | Maniero | A47J 27/04 | 219/679 |
| 5,370,222 A * | 12/1994 | Steigerwald | B65D 81/3205 | 206/219 |
| 5,419,445 A | 5/1995 | Kaesemeyer | | |
| 5,505,917 A * | 4/1996 | Collier, Jr. | A61L 2/04 | 422/307 |
| 5,676,128 A | 10/1997 | Cowart | | |
| 5,794,802 A * | 8/1998 | Caola | A61J 1/2093 | 206/219 |
| 5,890,627 A * | 4/1999 | Storey | B65D 25/04 | 222/129 |
| 6,036,918 A * | 3/2000 | Kowanko | A01N 37/16 | 422/33 |
| 6,045,254 A * | 4/2000 | Inbar | A61J 9/00 | 366/130 |
| 6,089,389 A * | 7/2000 | Sharon | A61J 9/00 | 141/9 |
| 6,113,257 A * | 9/2000 | Sharon | A61J 9/00 | 206/221 |
| 6,485,979 B1 * | 11/2002 | Kippenhan | A61L 2/24 | 422/403 |
| 6,739,465 B1 * | 5/2004 | Calvert | A61J 9/00 | 215/11.1 |
| 6,820,767 B2 * | 11/2004 | Nicholas | A47G 19/2205 | 222/132 |
| 7,150,369 B1 * | 12/2006 | Fryar | A61J 9/00 | 215/11.4 |
| 7,798,346 B2 * | 9/2010 | Nelson | B65D 81/3205 | 206/501 |
| 7,850,027 B2 * | 12/2010 | Hayes | A61J 9/00 | 206/219 |
| 7,992,735 B2 * | 8/2011 | Bullard | B65D 81/3222 | 206/221 |
| 8,151,985 B2 * | 4/2012 | Owoc | B65D 25/08 | 206/219 |
| 8,459,450 B1 * | 6/2013 | Whitaker | A61J 9/00 | 206/219 |
| 8,556,094 B2 * | 10/2013 | Brown | A61J 1/2093 | 206/219 |
| 8,899,427 B2 * | 12/2014 | Harris | A61J 9/00 | 206/219 |
| 9,016,488 B1 * | 4/2015 | Peres | B65D 81/3205 | 206/219 |
| 9,156,589 B2 * | 10/2015 | Fernandez de Castro | B65D 25/08 | |
| D750,968 S * | 3/2016 | Marseglia | D24/197 | |
| 9,629,782 B2 * | 4/2017 | Hayes | A61J 9/008 | |
| 2002/0064478 A1 * | 5/2002 | Davis | A61L 2/26 | 422/26 |
| 2007/0253864 A1 * | 11/2007 | Maguire, Jr. | A61L 2/14 | 422/28 |
| 2012/0205269 A1 * | 8/2012 | Ludvig | A61B 19/026 | 206/363 |
| 2013/0022727 A1 * | 1/2013 | Sherwin | F24S 30/425 | 426/523 |
| 2015/0208848 A1 * | 7/2015 | Huang | A47J 27/21166 | 99/403 |
| 2015/0217008 A1 * | 8/2015 | Zwingenberger | A61L 2/07 | 134/25.1 |

* cited by examiner

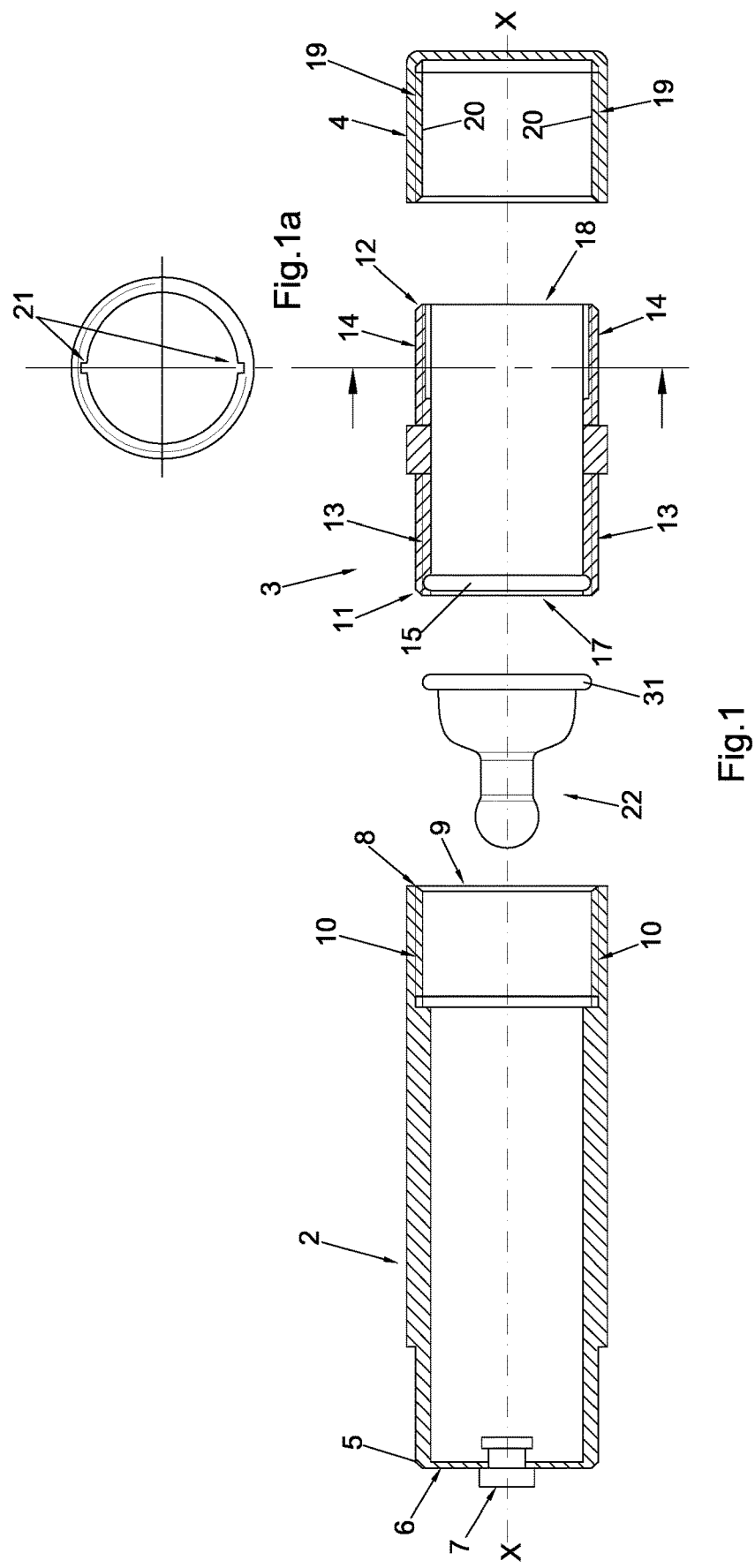

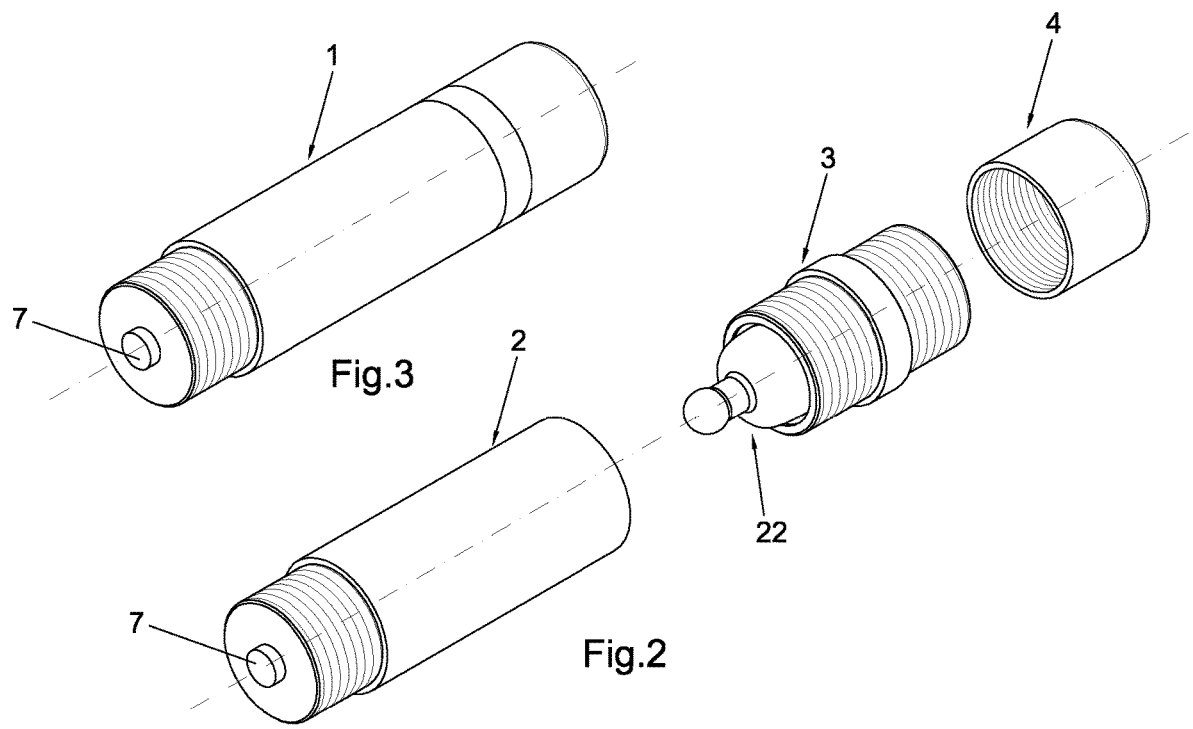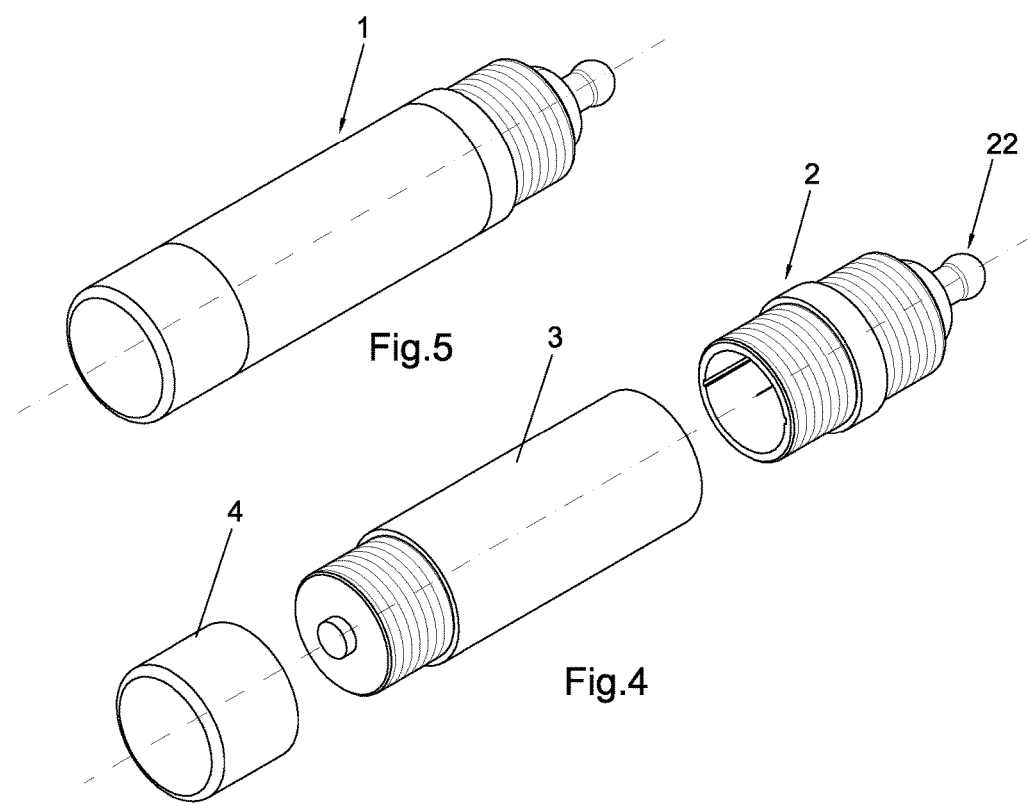

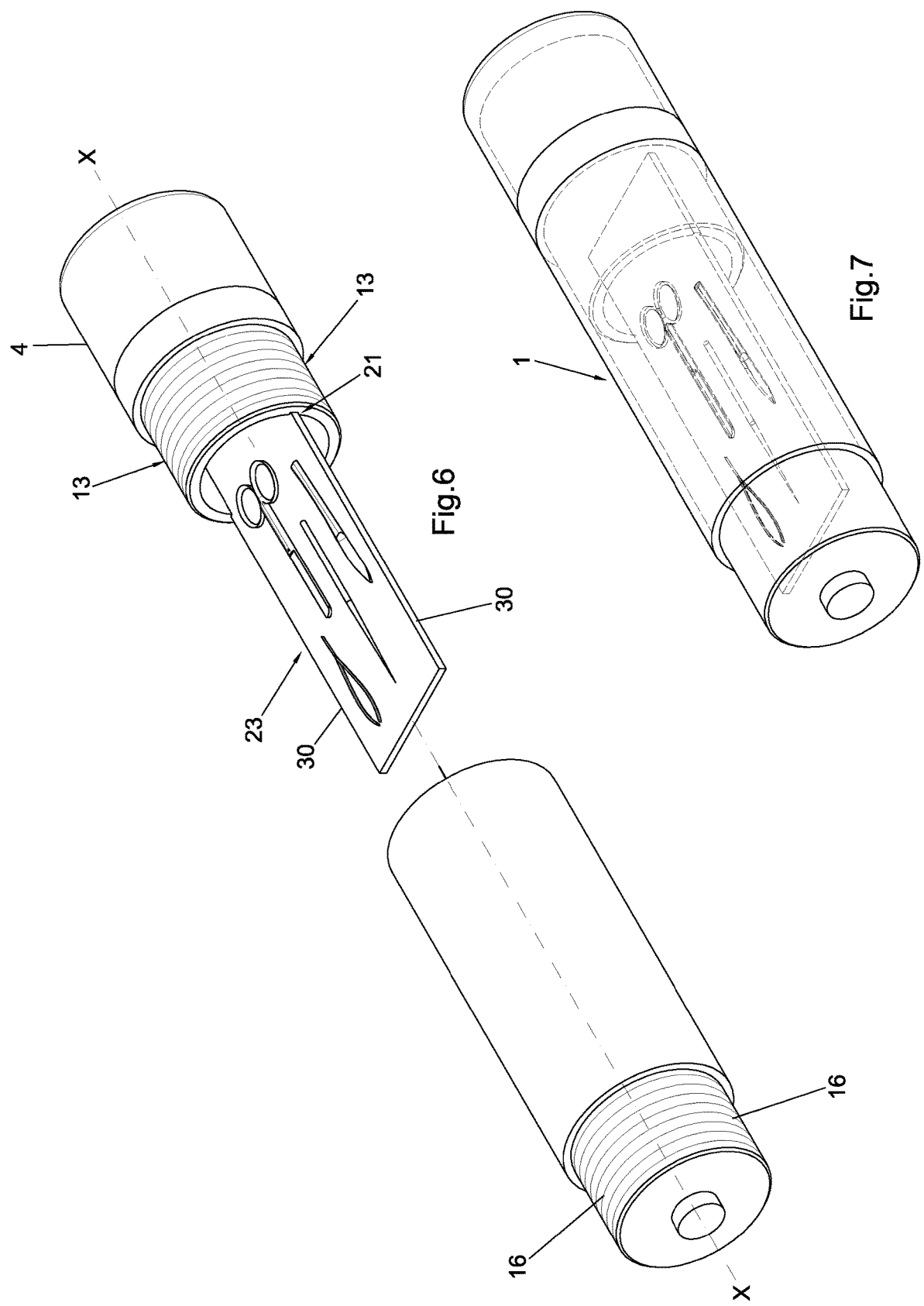

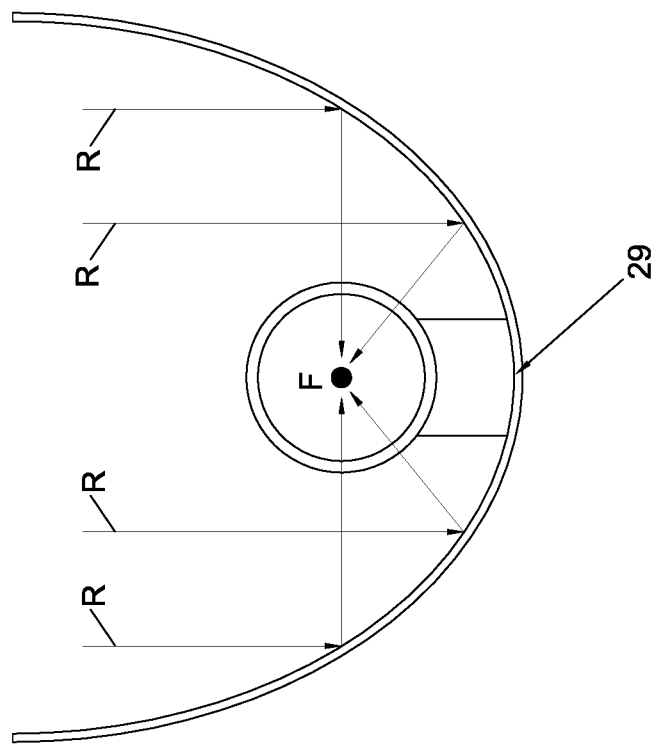
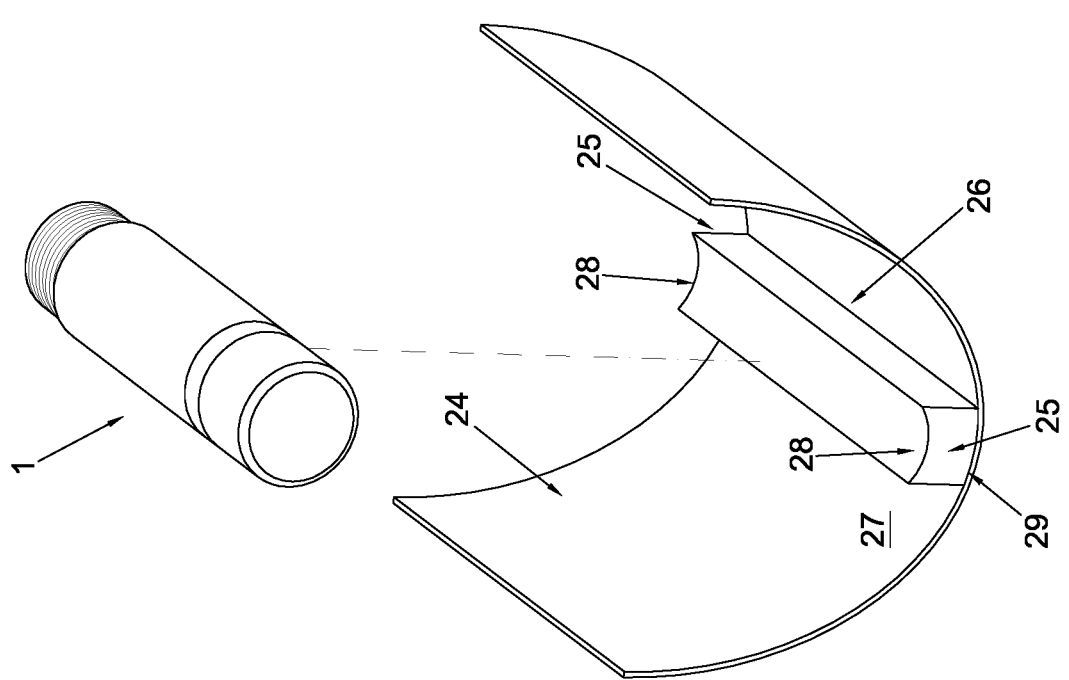

CONTAINER FOR STERILISING OBJECTS AND STERILISING SYSTEM COMPRISING SAID CONTAINER

BACKGROUND OF THE INVENTION

1. Field of the Invention

The present invention concerns a container for sterilising objects, suited to sterilise both liquids and objects contained inside it.

2. Present State of the Art

Several sterilising processes of the physical or chemical type are known.

In general, in the sterilisation process carried out with physical means the action of heat is used. In this case it is necessary to have a heat source that is such as to heat the device to be sterilised.

In the sterilisation process carried out with chemical means, instead, ethylene oxide, ozone, propylene oxide, methyl bromide, peroxyacetic oxide are generally used.

The addition of chemical substances as sterilisers, however, is not very widespread, since generally these substances exert an inhibiting action rather than a true sterilising action.

Furthermore, once added, gaseous substances are difficult to eliminate and can give the treated product unpleasant smell and taste characteristics.

Today in the industrial sector the sterilisation process is carried out through the following operations:
  preparation of the raw material to be sterilised;
  filling of the containers with the objects to be sterilised and elimination of the air present therein;
  tight sealing of the containers and heat treatment of the containers sealed in this way in autoclave or through a system for transporting the sealed containers on belts;
  rapid cooling of the containers.

Sterilisation performed in autoclave requires a system constituted by:
  an accumulation tank intended to store a certain quantity of water;
  a pump with suitable delivery and head;
  a pressurised container containing an air space;
  a pressure switch, meaning a switch capable of operating the pump according to the water pressure.

Therefore, in the case of the autoclave, a complex system is needed, which requires the use of several components.

Differently, a device using solar energy for cooking and sterilising liquids or articles is illustrated in U.S. Pat. No. 5,676,128.

Some sterilising storage containers are present in the patent's literature as in GB 2 048 676, which illustrates a sterilising storage container device for dental tools supported for sterilisation by heat or chemical processes, and in EP 1 555 034, which describes a receptacle and a process for sterilising and preserving the sterility of individual implements and instruments.

The document U.S. Pat. No. 5,419,445 illustrates a container for storing, mixing and dispensing in the form of a baby bottle.

A further drawback is due to the fact that it is often difficult to have such systems available, especially in the developing countries, in which technology is not as advanced as in the industrialised countries.

Another, yet not the least drawback, is represented by the fact that, especially in the developing countries, suitable heat sources are not always available to heat the objects or liquids to be sterilised.

SUMMARY OF THE INVENTION

The present invention intends to overcome said drawbacks.

In particular, it is the object of the present invention to provide a container for sterilising objects that can be made in a simple manner and at limited costs.

It is a further object of the present invention to provide a container for sterilising objects that can be easily used also in those countries where the level of technology is not very high.

Said objects are achieved by a container for sterilising objects whose main characteristics are in accordance with the teachings of the first claim.

Said objects are also achieved by a system for sterilising objects whose main characteristics are in accordance with the teachings of the other independent claim.

Further characteristics and details of the invention are the subject of the dependent claims.

Advantageously, the container according to the invention is easy to build and has low production costs.

Still advantageously, the sterilising system according to the invention avoids the use of gas as heating source for the system itself and therefore can be used also in the developing countries.

Still advantageously, the container according to the invention, in addition to assuming a sterilisation configuration, can also assume a configuration of use in which it becomes a baby bottle ready for use.

Still advantageously, in the container according to the invention the passage from the configuration of sterilisation to the configuration of use takes place through a simple manual operation in which the components making up the container are unscrewed.

BRIEF DESCRIPTION OF THE DRAWINGS

Said objects and advantages are highlighted in greater detail in the description of a preferred embodiment of the invention that is provided by way of non-limiting example with reference to the attached drawings, wherein:

FIG. 1 shows a sectional and exploded view of a container for sterilising objects according to the invention;

FIG. 1a shows a sectional view of a detail of FIG. 1;

FIG. 2 shows an exploded axonometric view of the container of FIG. 1 with an object to be sterilised;

FIG. 3 shows a view of the container of FIG. 2 assembled;

FIG. 4 shows an exploded axonometric view of the container of FIG. 2 in the configuration of use;

FIG. 5 shows an axonometric view of the container of FIG. 4 assembled;

FIG. 6 shows an exploded axonometric view of a variant of the container of FIG. 2;

FIG. 7 shows an axonometric view of the container of FIG. 6 assembled;

FIGS. 8 and 9 respectively show an axonometric view and a front view of a sterilising system according to the invention;

DETAILED DESCRIPTION OF THE PREFERRED EMBODIMENTS

Figure 10:
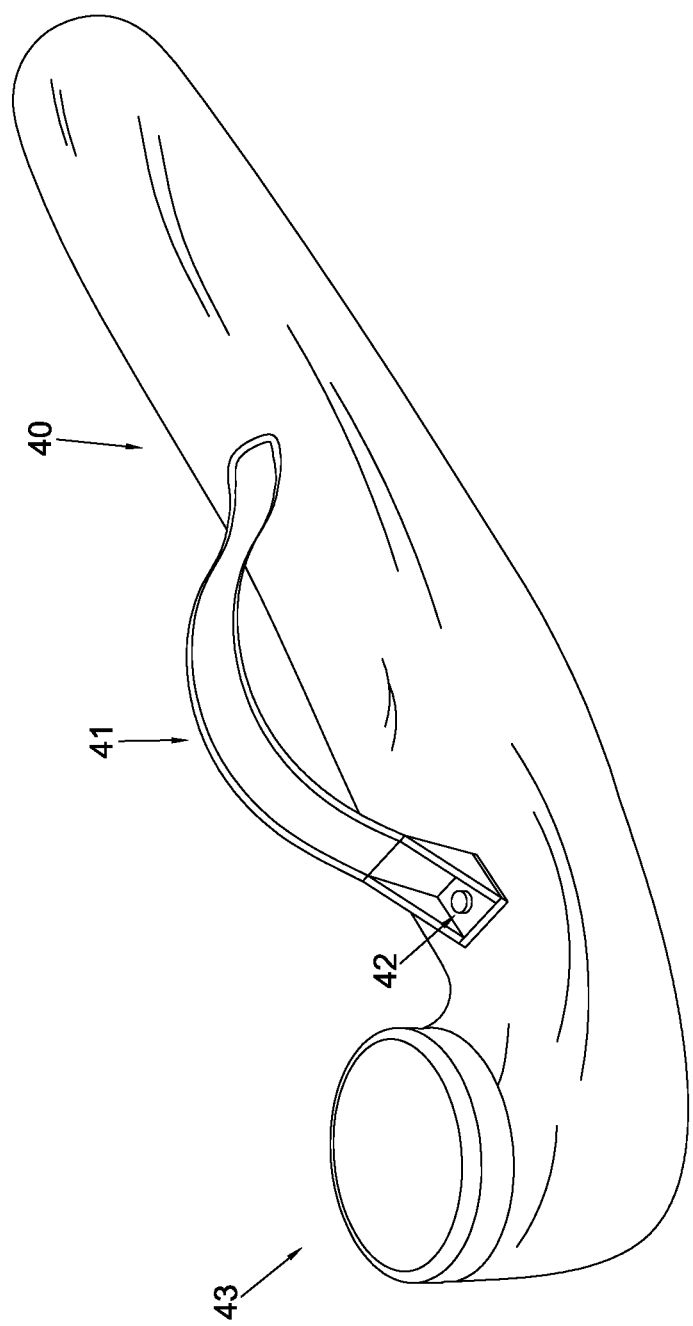
FIG. 10 shows an axonometric view of a construction variant of the container of FIG. 1.

With reference to FIG. 1, the container according to the invention, indicated as a whole by 1, comprises:
- a hollow body 2 with mainly longitudinal development;
- a substantially tubular body 3;
- a shaped cover 4;
- supporting means arranged inside the tubular body 3 and configured to support one or more objects to be sterilised.

According to the present invention, the hollow body 2, the tubular body 3 and the shaped cover 4 can be coupled together in order to define the container 1, inside which it is possible to identify a volume that can be filled with a liquid in order to sterilise the liquid itself and the objects contained in the container.

In particular, always according to the present invention, the hollow body 2 is closed at the end 5 by a bottom 6 provided with a maximum pressure valve 7 and at the opposite end 8 it is provided with an opening 9 in proximity to which there is a first connection area 10.

Always according to the present invention and with reference to FIG. 1, in proximity to its ends 11 and 12 the tubular body 3 is respectively provided with a second connection area 13 and with a third connection area 14, each one of which can alternatively be coupled with the first connection area 10 of the hollow body 2.

The coupling method will be explained in greater detail below.

In particular, and with reference to FIG. 1, the first connection area 10 is constituted by an inner thread, and therefore a female thread.

Concerning the tubular body 3, at the level of its openings 17, 18 the second and the third connection areas 13 and 14 are respectively constituted by two external male threads.

Finally, concerning the shaped cover 4, this is provided with a fourth connection area 19 constituted by an inner thread made in the inner walls 20 of the cover 4.

In the detail of FIG. 1a it is possible to observe the means for supporting the objects, consisting of longitudinal channels 21 obtained on the inner thread of the fourth connection area 19 of the tubular body 3.

The longitudinal channels 21 are configured so as to support one or more objects, for example an object tray 23 suited to contain surgical instruments and shown in FIGS. 6 and 7.

In the case where the longitudinal channels 21 are used, the tray 23 is inserted in them with its lateral edges 30.

Preferably but not necessarily, the tray 23, in addition to being supported by the longitudinal channels 21, can be supported also by fixing means (not visible in the figure) that project from the inner surfaces of the container 1.

With reference to FIG. 2, it shows a sterilisation configuration in which the container 1, once it has been filled with water or another liquid, sterilises the nipple 22 of a baby bottle.

It can be observed in FIG. 1 that the nipple 22 is coupled with the container 1 by fitting its ring 31 in an annular recess 15 obtained in the tubular body 3.

FIGS. 4, 5, 6, and 7, instead, show a configuration of use in which the container 1 is changed into a baby bottle (FIG. 5) or a device for supporting the object tray 23 (FIG. 7). Channels 21, tray 23 and recess 15 are herein examples of support means for supporting one or more objects to be sterilised.

The passage from the sterilisation configuration, shown in FIG. 2, to the configuration of use shown in FIGS. 4 and 5 is explained in greater detail below.

With reference to FIG. 8, the container 1 is a component part of a sterilising system comprising a parabolic mirror 24 and two plate-like supporting elements 25 suited to support the container 1.

As can be observed in FIG. 8, a supporting frame is provided that comprises two plate-like supporting elements 25 spaced from and parallel to each other, joined by a connection element 26 that connects them defining a U-shaped structure.

With reference to FIGS. 8 and 9, each plate-like supporting element 25 is hinged to the surface 27 of the parabolic mirror 24 and is provided with a concave surface 28 configured so that it houses the container 1.

Advantageously, the concave surfaces 28 are configured in such a way that they can be coupled with the cylindrical outline of the container 1.

With reference to FIGS. from 1 to 7, the container according to the invention operates as follows.

The ring 31 of the nipple 22 of a baby bottle to be sterilised is fixed to the annular recess 15 of the tubular body 3.

The tubular body 3 is connected to the hollow body 2 by coupling the matched profiles of the male threads of the second connection area 13 of the tubular body 3 with those of the female thread of the first connection area 10 of the hollow body 2.

An inner volume is thus created that is filled with water or another liquid to be sterilised through the opening 18.

Finally, the opening 18 is closed by coupling the matched profiles of the male threads of the third connection area 14 of the tubular body 3 with the female thread of the inner walls 20 of the shaped cover 4. This coupling operation produces the container 1 visible in FIG. 3.

The container 1 is then heated by means of a heat source (not visible in the figure), for example by means of gas burners.

The heat emitted by the gas burners heats the water to be sterilised contained in the container 1.

Once the sterilisation temperature (generally about 130° C.) has been reached, the valve 7 is activated and signals that the sterilisation step has been completed.

At this point, the container 1 is opened by unscrewing the cover 4 and placing it near the container.

Successively, the tubular body 3 is unscrewed from the hollow body 2 and is overturned, in such a way that the nipple 22 coupled with it through the annular recess 15 faces towards the outside.

The final configuration that is obtained is represented in FIG. 5 and is a configuration of use in which the container 1 is changed into a real baby bottle ready to be used.

In the case where the object tray 23 needs to be sterilised instead of the nipple 22, the sterilising procedure will be analogous to that which has been described above.

The container 1 will then be unscrewed, as explained above, in order to obtain a supporting device for an object tray 23 ready to be used, sterilised together with the objects contained in it and visible in FIG. 6.

Therefore, to advantage, it is possible to comfortably pass from a configuration of sterilisation to a configuration of use by simply unscrewing the components of the container according to the invention by hand.

FIG. 10 shows a variant embodiment of the container for sterilisation according to the invention, now indicated by 40, which differs from the preceding embodiment in that the container 40 is provided with a carrying handle 41.

Furthermore, it is always provided with a maximum pressure valve 42 that now is no more positioned in proximity to the bottom of the container, but is positioned inside the handle 41, near one of its ends.

Advantageously, the fact that the valve 42 is applied in proximity to the handle 41 prevents it from being damaged in case the container 40 should accidentally fall on the ground.

Advantageously, the container 40, thanks to the handle 41 with which it is provided, can be easily carried by the user and rested on a heat source (not visible in the figure), for example on embers, in order to sterilise it.

The container 40 always comprises a hollow body, a tubular body and a cover 43 that can be screwed and unscrewed.

As in the case of the container 1, also in this case the tubular body (not visible in the figure) of the container 40 is provided with an annular recess (not visible in the figure) suited to house the nipple of a baby bottle.

The container 1, 40 can be inserted in a sterilisation system of the type described below and illustrated in FIGS. 8 and 9.

For the sake of simplicity, FIGS. 8 and 9 show the sterilisation system only with reference to the container 1, but that which is described below applies also to the container 40.

Said system, with reference to FIGS. 8 and 9, comprises:
a parabolic mirror 24;
the container 1;
two plate-like supporting elements 25, spaced from each other and hinged, at the level of their base 29, to the surface 27 of the parabolic mirror 24.

The plate-like supporting elements 25 are configured so as to support the container 1 during its sterilisation.

The assembly of said sterilisation system is carried out as follows.

The container 1 is positioned on the plate-like supporting elements 25 after it has been filled with water to be sterilised and the nipple 22 or the tray 23 to be sterilised has been introduced inside it.

At this point, the energy of sun rays is exploited to heat the container 1.

As the parabola is defined as the geometrical place of the points of a plane that are equidistant from a fixed point called focus and a straight line called directrix, the container 1 is positioned in such a way that the focus F of the parabolic mirror 24 is located on the longitudinal axis X of the container 1.

In fact, all the sun rays R are reflected towards the focus F of the mirror 24 and therefore on the longitudinal axis X of the container 1.

In this way, the liquid and the objects contained in the container 1 are sterilised with no need to use gas burners or similar heat sources.

Once said system has been used, it can be removed from the parabolic mirror which is then folded and is ready to be transported to and used in another place.

As can be seen, advantageously, the sterilisation system just described above is easy to produce and also to use.

Still advantageously, the sterilisation system according to the invention can be used with no need to use chemical substances or install complex equipment.

As can be understood from the description provided above, the container and the sterilisation system according to the invention achieve the set objects.

In the construction step, the container and the sterilisation system according to the invention can be subjected to modifications that must be considered protected by the present patent, provided that they fall within the scope of the following claims.

The invention claimed is:

1. A container for sterilising objects, comprising:
an elongated hollow body having a closed end and an opposing first open end, said first open end having a first connection area;
a tubular body having a second open end and an opposing third open end, said second open end having a second connection area and said third open end having a third connection area, said second and third connection areas being configured to alternatively directly couple with said first connection area; —a shaped cover provided with a fourth connection area, the fourth connection area being configured to directly couple alternatively with one of said second or third connection areas of said tubular body or with said first connection area of said hollow body;
supporting elements arranged inside said tubular body for supporting one or more objects to be sterilized, the supporting elements comprising longitudinal channels and an object tray configured to be supported by the longitudinal channels, and
a maximum pressure valve mounted on the hollow body, wherein said container is capable of being assembled into a first configuration and a second configuration, the first configuration being configured for sterilization of the one or more objects, and the second configuration being configured for allowing a user to access the one or more objects, wherein in said first configuration:
said tubular body is directly coupled to said shaped cover by connecting said third connection area to said fourth connection area,
said tubular body is directly coupled to said hollow body by connecting said second connection area to said first connection area such that said one or more objects is contained inside the container when the one or more objects is supported by said supporting elements and such that the container bounds a volume that can be filled with liquid to sterilize the one or more objects when the one or more objects is supported by said supporting elements; and wherein in said second configuration: said hollow body is directly coupled to said tubular body by connecting said first connection area to said third connection such that said one or more objects when supported by said supporting elements are openly exposed to the outside for access by a user, and wherein said container is a baby bottle.

2. The container for sterilising objects according to claim 1, wherein said first connection area of said hollow body is a female thread.

3. The container for sterilising objects according to claim 1, wherein said second and said third connection area of said tubular body are two male threads.

4. The container for sterilising objects according to claim 1, wherein said fourth area of said cover is a female thread.

5. The container for sterilising objects according to claim 1, wherein in said second configuration, said shaped cover is coupled with said hollow body by connecting said fourth connection area and said second connection area.

6. The container for sterilising objects according to claim 1, wherein the supporting elements arranged inside said tubular body for supporting said one or more objects to be sterilized comprises a tray disposed within the tubular body.

7. The container for sterilising objects according to claim 1, further comprising the one or more objects, the one or more objects comprising a bottle nipple supporting by the supporting elements.

8. The container for sterilising objects according to claim 7, wherein the bottle nipple projects into the hollow body when the container is in the first configuration.

9. The container for sterilising objects according to claim 1, wherein when the container is in the first configuration, the first connection and the second connection are threadedly coupled together.

10. The container for sterilising objects according to claim 9, wherein when the container is in the first configuration, the third connection and the fourth connection are threadedly coupled together.

11. The container for sterilising objects according to claim 9, wherein when the container is in the second configuration, the fourth connection of the shaped cover is threadedly coupled to the closed end of the hollow body.

12. A container for sterilising objects, comprising:
an elongated hollow body having a closed end and an open end opposing first open end;
a tubular body having a second open end and an opposed third open end, the second open end and the third open end being configure to alternatively directly couple with the first open end;
a shaped cover provided with a fourth open end, the fourth open end being configured to directly couple with one of the second open end or, alternatively, third open end of the tubular body and with the hollow body;
supporting elements arranged inside said tubular body for supporting one or more objects to be sterilized, the supporting elements comprising longitudinal channels and an object tray configured to be supported by the longitudinal channels;
a maximum pressure valve mounted on the hollow body; and
a bottle nipple secured to the tubular body so as to outwardly project from the second open end of the tubular body;
wherein the container is capable of being assembled into a first configuration, a second configuration, a third configuration and a fourth configuration, wherein in the first configuration:
the third open end of the tubular body is threadedly directly coupled to the fourth open end of the shaped cover, and the second open end of the tubular body is threadedly directly coupled to the first open end of the hollow body so that the bottle nipple projects into the hollow body; and
wherein in the second configuration:
the third open end of the tubular body is threadedly directly coupled to the first open end of the hollow body so that the bottle nipple is openly exposed to the outside and
wherein in the third configuration:
said tubular body is directly coupled to said hollow body by connecting said second open end to said open end of the hollow body such that said one or more objects is contained inside the container when the one or more objects is supported by said supporting elements and such that the container bounds a volume that can be filled with liquid to sterilize the one or more objects when the one or more objects is supported by said supporting elements; and
wherein in said fourth configuration;
said hollow body is directly coupled to said tubular body by connecting said open end of the hollow body to said third open end of the tubular body such that said one or more objects when supported by said supporting elements are openly exposed to the outside for access by a user.

13. A container for sterilising objects, comprising:
an elongated hollow body having a closed end and an opposing first open end, said first open end having a first connection area;
a substantially tubular body having a second open end and a third open end opposed to the second open end, said second open end having a second connection area and said third open end having a third connection area opposed to the second connection area, said second and third connection areas being provided each one with a respective threading and configured to alternatively directly couple with said first connection area;
a shaped cover provided with a fourth connection area, the fourth connection area being configured to directly couple with one of said second or third connection areas of said tubular body and with said first connection area of said hollow body;
supporting elements arranged inside said tubular body for supporting one or more objects to be sterilized, the supporting elements comprising longitudinal channels and an object tray configured to be supported by the longitudinal channels, and
a maximum pressure valve mounted on the hollow body,
wherein said container is capable of being assembled into a first configuration and a second configuration, the first configuration being configured for sterilization of the one or more objects, and the second configuration being configured for allowing a user to access the one or more objects, wherein in said first configuration:
said tubular body is directly coupled to said shaped cover by connecting said third connection area to said fourth connection area, and
said tubular body is directly coupled to said hollow body by connecting said second connection area to said first connection area such that said one or more objects is contained inside the container when the one or more objects is supported by said supporting elements and such that the container bounds a volume that can be filled with liquid to sterilize the one or more objects when the one or more objects is supported by said supporting elements; and wherein in said second configuration:
said hollow body is directly coupled to said tubular body by connecting said first connection area to said third connection are such that said one or more objects when supported by said supporting elements are openly exposed to the outside for access by a user and
wherein said container is a baby bottle.

* * * * *